(12) United States Patent
Cannon et al.

(10) Patent No.: US 11,471,238 B2
(45) Date of Patent: Oct. 18, 2022

(54) MEDICAL WASTE CONTAINER

(71) Applicant: Wake Forest University Health Sciences, Winston-Salem, NC (US)

(72) Inventors: Michael L. Cannon, Lewisville, NC (US); Elizabeth Carter, Advance, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 16/709,194

(22) Filed: Dec. 10, 2019

(65) Prior Publication Data
US 2020/0179076 A1    Jun. 11, 2020

Related U.S. Application Data

(60) Provisional application No. 62/777,342, filed on Dec. 10, 2018.

(51) Int. Cl.
*A61M 5/32* (2006.01)
*A61B 50/36* (2016.01)
*B65D 25/14* (2006.01)
*A61B 50/00* (2016.01)

(52) U.S. Cl.
CPC ......... *A61B 50/362* (2016.02); *A61M 5/3205* (2013.01); *B65D 25/14* (2013.01); *A61B 2050/0051* (2016.02); *A61B 2050/0058* (2016.02); *A61B 2050/364* (2016.02)

(58) Field of Classification Search
CPC .................. A61B 50/362; A61B 50/36; A61B 2050/0051; A61B 2050/0058; A61B 2050/364; A61M 5/3205
USPC .................................................. 206/370, 438
See application file for complete search history.

(56) References Cited

U.S. PATENT DOCUMENTS

| 4,995,871 | A | * | 2/1991 | Sasaki | A61M 5/3205 206/366 |
|---|---|---|---|---|---|
| 6,247,592 | B1 | * | 6/2001 | Racicot | A61M 5/3205 206/366 |
| 8,348,056 | B2 | * | 1/2013 | Maness | A61B 50/362 206/366 |
| 2009/0266729 | A1 | * | 10/2009 | Alcouloumre | B65D 83/0847 206/370 |
| 2017/0209230 | A1 | * | 7/2017 | Nakagami | A61B 50/362 |

OTHER PUBLICATIONS

Overview of Eight Medicine Disposal Products, Community Environmental Health Strategies LLC for San Francisco Department of the Environment, Apr. 21, 2017, 48 pages.

\* cited by examiner

*Primary Examiner* — King M Chu
(74) *Attorney, Agent, or Firm* — Kilpatrick Townsend & Stockton LLP

(57) ABSTRACT

Disclosed is a waste container comprising a port in communication with a tube where the port is configured to receive a fluid from an implement and the tube is configured to direct the fluid from the implement toward an absorbent material within the waste container.

20 Claims, 13 Drawing Sheets

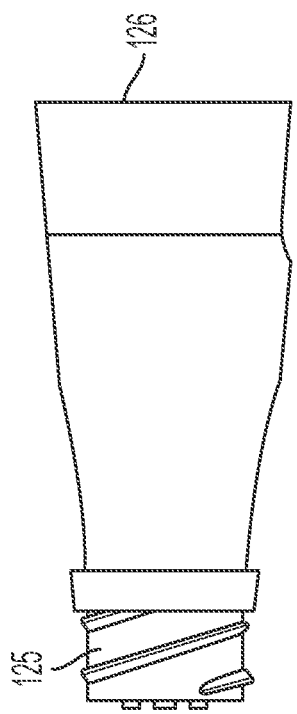
FIG. 11

MEDICAL WASTE CONTAINER

RELATED APPLICATIONS

This application claims the benefit of priority to U.S. Provisional Patent Application Ser. No. 62/777,342, filed Dec. 10, 2018, the contents of which are hereby incorporated by reference as if recited in full herein.

FIELD

The presently disclosed subject matter relates to containers for safe disposal of implements. In certain embodiments, the container may be used in clinical settings.

BACKGROUND

Medical waste containers, also known as sharps containers, can be used for safe disposal of syringes, needles, and other implements used in clinical settings. A syringe may contain residual medication after treatment of a patient. In some cases, the amount of residual medication may be significant depending on the initial loading of the syringe and the amount of medication administered to a patient. Blood or other bodily fluids may be within the syringe or on the external surface of the syringe. Medical waste containers can provide a designated disposal location to prevent undesired contact of persons with a used syringe and protect them from the dangers posed by contact with the residual medication, bodily fluids, or infectious diseases.

In many units of a clinical setting, such as an intensive care unit (ICU), trauma unit, operating room or procedure suite, or emergency room, the medications used may be controlled substances, including narcotics and opioids. Often, medical waste containers in these units remain open and accessible to personnel to aid in the speed of disposal of medical implements. However, the syringes and other implements with residual amounts of these controlled substances can be stolen and serve as a source for illegal sale or use of these highly addictive substances. To combat this issue, medical personnel often discharge remaining amount of the controlled substances from the syringe prior to disposal of the syringe. Discharging these substances in an ordinary sink drain potentially contaminates water supplies and consumes precious time from critical patient care. Discharge into a trash can exposes personnel to potentially infectious agents and may allow diversion of controlled substances. Thus, these practices are avoided. Often, any remaining amount of the controlled substances is discharged from the syringe directly into a medical waste container prior to disposing the syringe into the container. This practice remedies the concern of syringes with residual amounts of controlled substances and/or bodily fluids with infectious diseases to be stolen for illicit use. However, this practice introduces risks to medical personnel discharging the residual medications into a container. The contents of a syringe can splash or splatter off the wall of the container or other syringes or implements within the container. In some cases, clothing or skin of medical personnel can be inadvertently sprayed, posing risk of adverse reaction to medications or exposure to infectious disease from the bodily fluids. Thus, there is a need to develop medical waste containers that can be used for the safe disposal of syringes and other implements containing residual medications and/or bodily fluids.

SUMMARY

In some embodiments, a waste container can comprise a vessel comprising a base and at least one sidewall, where the at least one sidewall is connected to the base. An interior volume of the vessel may be defined by the at least one sidewall and base. The vessel can further comprise a port having a first side and a second side, where the first side faces an exterior of the vessel and the second side faces the interior volume of the vessel. The vessel can further comprise a tube coupled to the second side of the port. The tube may be configured to direct a fluid from an implement toward the interior volume of the vessel, and in certain embodiments the tube may direct the fluid toward a targeted area. In certain embodiments, an absorbent material can be positioned within the interior volume of the vessel and may be a targeted area for transport of the fluid. In some embodiments, the waste container can further comprise a cover configured to connect to the at least one sidewall and enclose the interior volume of the vessel. The cover can define an opening and provide for the vessel to receive a plurality of implements through the opening.

In certain embodiments, the port may comprise an adaptor compatible with a discharge end of the implement. The adaptor can include a Luer lock, where the Luer lock can mate with an end of a syringe. Optionally, the container can include a shield around the port. In some embodiments, the absorbent material can include a gel. The fluid can include a bodily fluid, a pharmaceutical composition, or a combination thereof.

Also disclosed is a method of using a waste container, comprising discharging a fluid from an implement through a port into a vessel. The port may be positioned in a cover for the vessel, and the port may couple to a tube that extends into the vessel. The method may further comprise disposing of the implement into the vessel through an opening defined by the cover. Optionally, the method may comprise connecting the implement to an adaptor positioned on the port, where the adaptor is compatible with a discharge end of the implement.

BRIEF DESCRIPTION OF THE DRAWINGS

FIG. 11 is a side view of an adaptor for a medical waste container according to one embodiment described herein.

DETAILED DESCRIPTION

Figure 1:
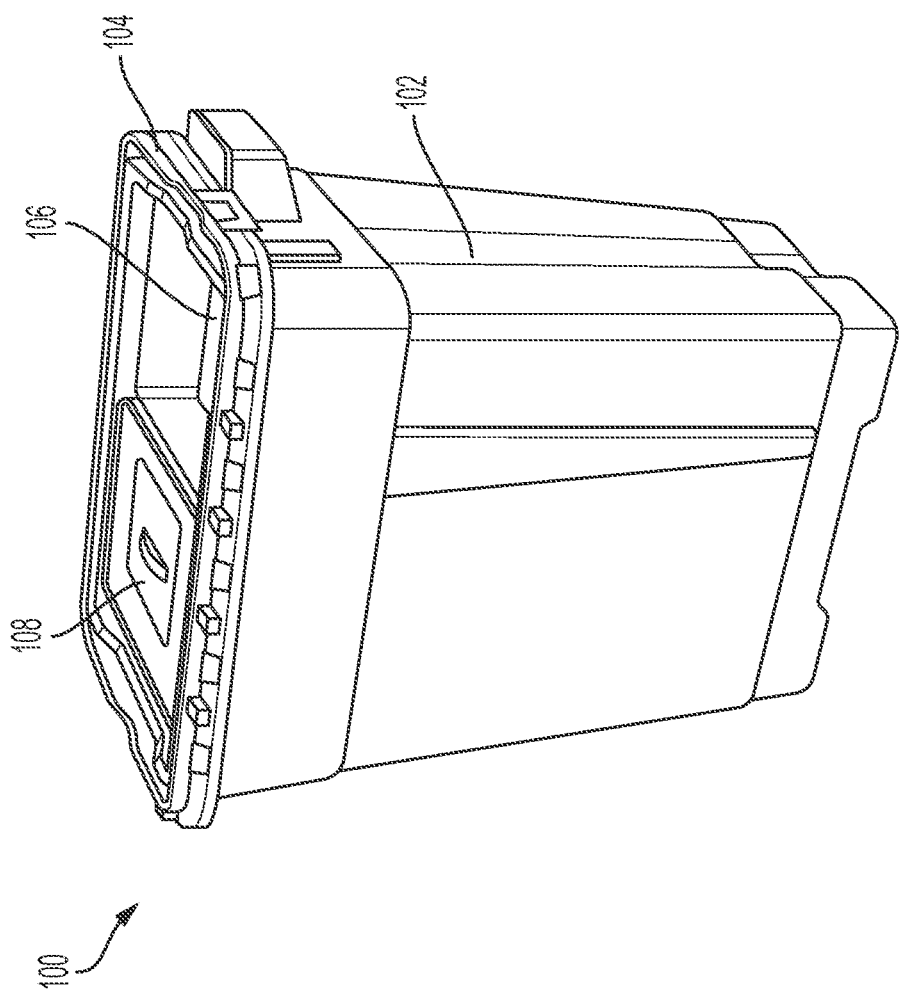
FIG. 1 is a perspective view of a comparative medical waste container.

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Described herein are medical waste containers. The present disclosure may be embodied in a variety of ways. In one embodiment, the container may comprise a vessel comprising a base and at least one sidewall, where the at least one sidewall may be connected to the base. The base and at least one sidewall define an interior volume of the vessel. In some embodiments, the base can comprise a circular shape and include a single sidewall that encircles the base. In other embodiments, the base can comprise a polygonal shape. In certain embodiments, the base can comprise a substantially rectangular shape and include four sidewalls. In other embodiments, the base may be smaller in size than the cover, with the sidewalls tapering toward the base.

The container may comprise a cover configured to connect to the at least one sidewall and enclose the interior volume of the vessel. The cover may have a complementary shape to the sidewalls and interior volume of the vessel. In some embodiments, the cover defines an opening and the vessel may be configured to receive a plurality of implements through the opening. In some embodiments, the cover can comprise a gate configured to substantially seal the opening in a first position and provide access to the interior volume of the vessel in a second position. Optionally, the gate may slide or rotate from the first position to the second position.

The container may comprise an absorbent material positioned within an interior volume of the vessel. In some embodiments, the container may comprise a port configured to receive a fluid from an implement. The port may have a first side and a second side, where the first side faces an exterior of the vessel and the second side faces the interior volume of the vessel. The container may further comprise a tube coupled to the port, where the tube is configured to direct a fluid from an implement toward the absorbent material. In particular, the tube may be coupled to the second side of the port. In some embodiments, the tube may be rigid and fixed in place. In other embodiments, the tube may be flexible and may be positional within the vessel. The coupling of the tube to the port may be direct or indirect. The tube may be coupled by a removable connection, such as a threaded connection, quick connect connection, snap connection, or compression connection.

Turning to the figures, FIG. 1 shows a comparable medical waste container 100. A cover 104 is connected to the vessel 102. The cover 104 includes an opening 106 to dispose of medical implements within the vessel 102. The container 100 includes a gate 108 that may be positioned over the opening 106. The opening 106 may remain accessible to personnel to aid in the speed of disposal of medical implements in critical care units. Residual amounts of controlled substances discharged from a syringe directly into the waste container 100 prior to disposal of the syringe can splash or splatter off the wall of the container or other syringes or implements within the container.

Figure 2:
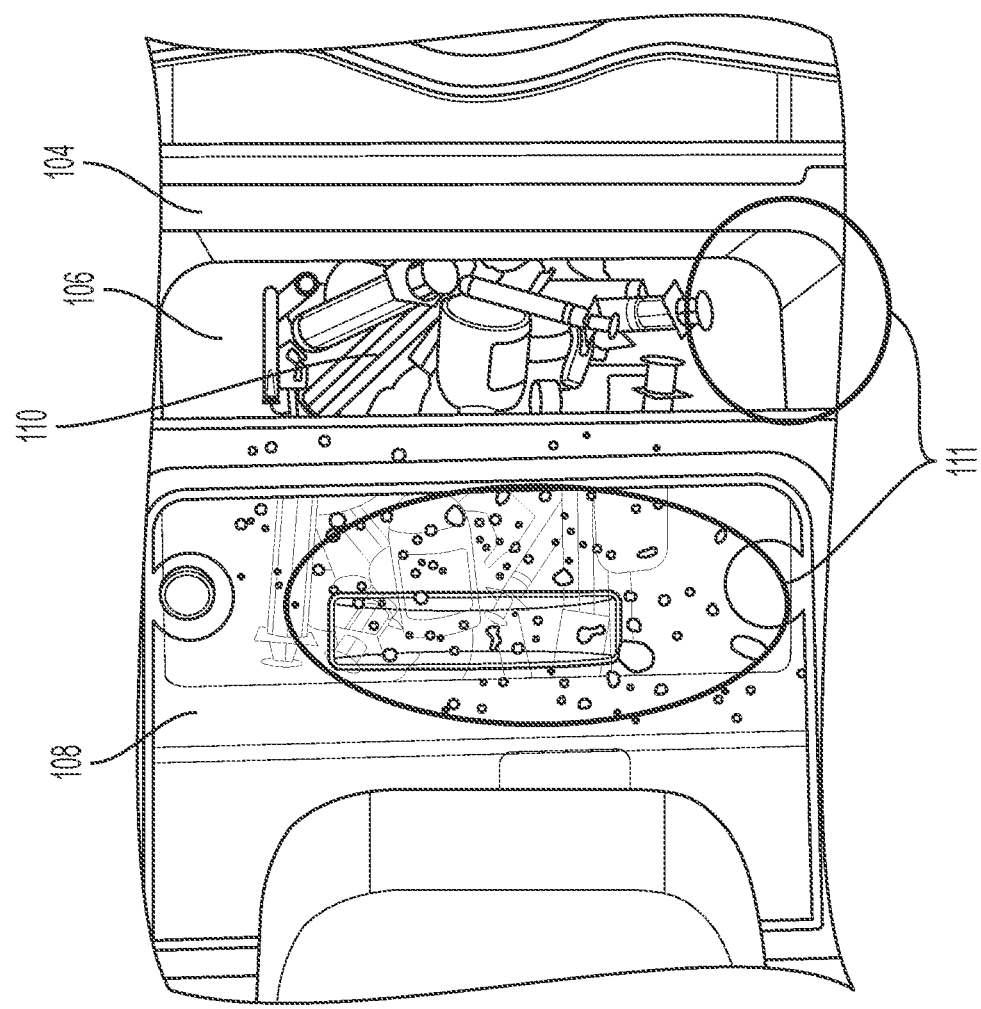
FIG. 2 is a top view of a comparative medical waste container.

FIG. 2 is a top view of a comparable medical waste container used in a critical care unit. As shown in FIG. 2, the gate 108 is partially closed, allowing the opening 106 to be accessible to personnel. Several implements and syringes 110 were previously disposed in the container 100. Splatter 111, is visible on the gate 108 and cover 104 of the container 100.

Figure 3:
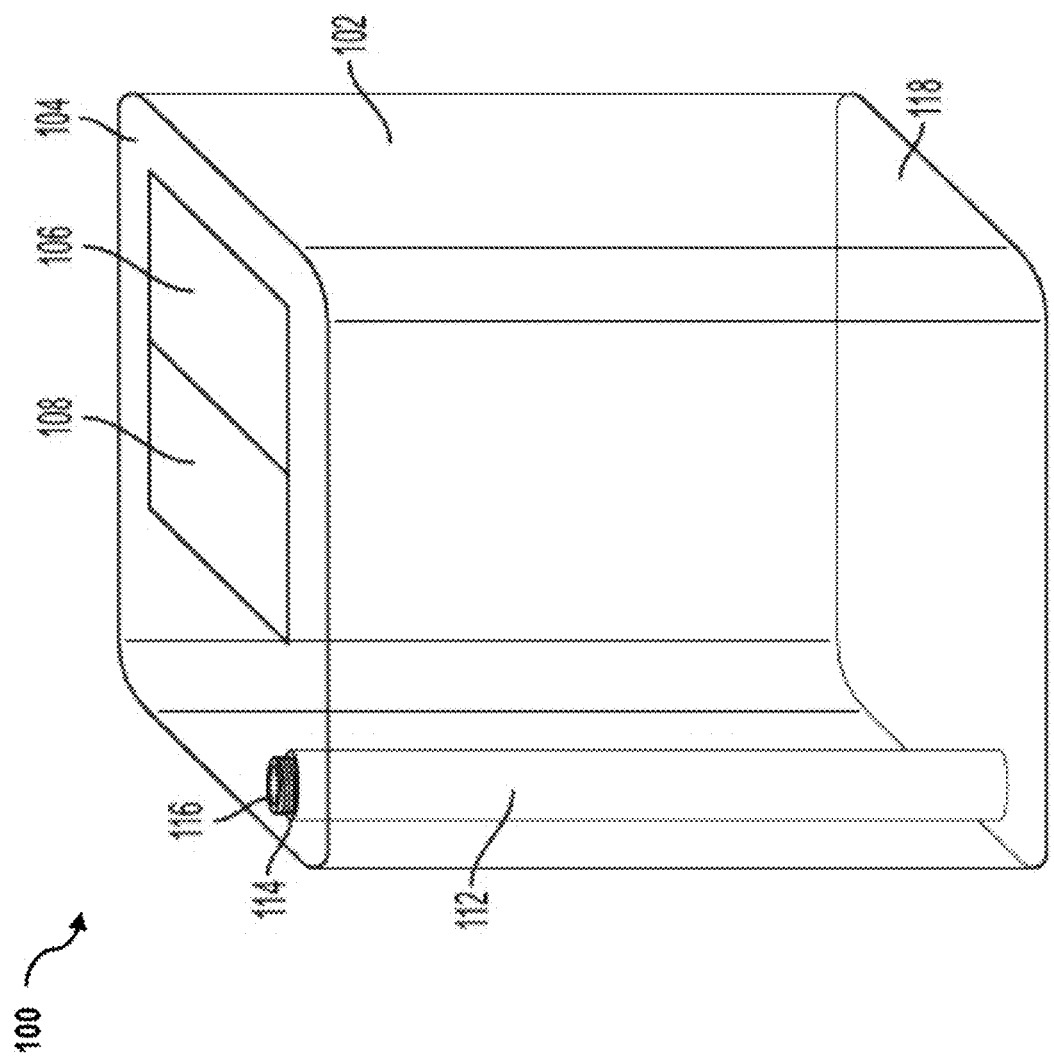
FIG. 3 is a perspective view of a medical waste container according to one embodiment described herein.
Figure 4:
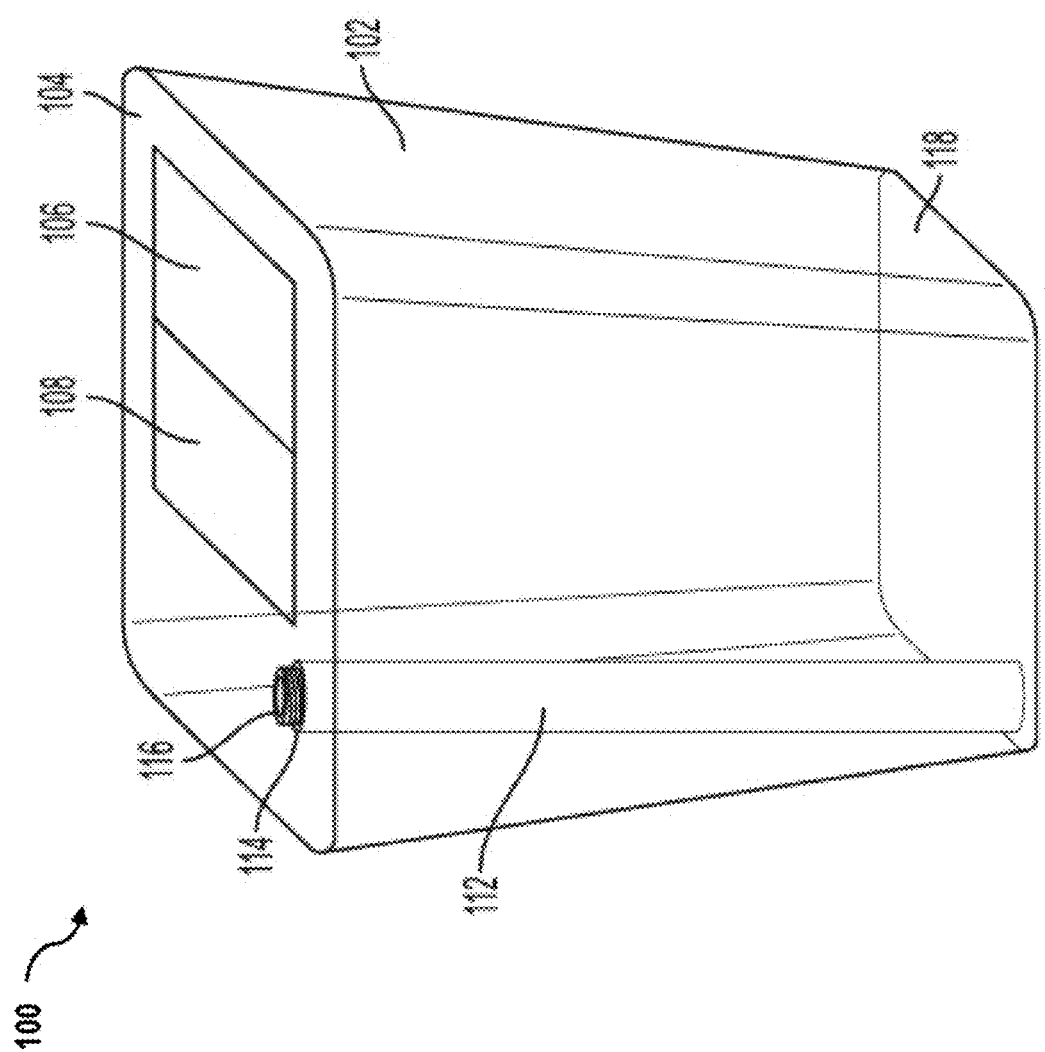
FIG. 4 is a perspective view of a medical waste container according to one embodiment described herein

FIG. 3 is a perspective view of a medical waste container 100 according to one embodiment of the present disclosure. FIG. 4 is a perspective view of a medical waste container 100 having tapered sidewalls according to one embodiment of the present disclosure. In FIGS. 3 and 4, the vessel 102 may be sized to hold a plurality of medical implements, such as syringes. The container may include a cover 104. In some examples, the cover may be removable from the vessel 102. The cover 104 may include an opening 106 and a gate 108. The gate may be configured to seal the opening in a first position and receive a plurality of implements through the opening in a second position. In some embodiments, the gate 108 may slide from the first position to the second position. In some embodiments, the gate 108 may rotate from the first position to the second position.

In some embodiments, a port 114 may be located in the cover 104. The port may be configured to receive a fluid from an implement and allow the fluid to pass into the interior volume of the vessel. In some embodiments, the port 114 may comprise an adaptor 116. The adaptor 116 may be compatible with a discharge end of the implement. In some embodiments, the adaptor 116 may be threaded. Optionally, the adaptor may comprise a Luer lock. In certain embodiments, the port may be configured with a self-sealing valve in which the tip of the implement may be inserted to discharge remaining fluid into the container through the tube.

In some embodiments, the container 100 may further comprise a tube 112 coupled to the port 114. The tube 112 may be configured to direct fluid from the implement toward bottom of the container 100. In certain embodiments, the tube 112 may be substantially perpendicular to the base 118 of the vessel 102. In some embodiments, a length of the tube 112 may be less than a length of the sidewall of the vessel 102. In some embodiments, the base 118 may be substantially rectangular, and the tube 112 may be adjacent to two sidewalls of the vessel 102, placing the tube vertically in a corner of the vessel 102, shown in FIG. 3. In some embodiments, the corners of the vessel may be curved or rounded.

Figure 5:
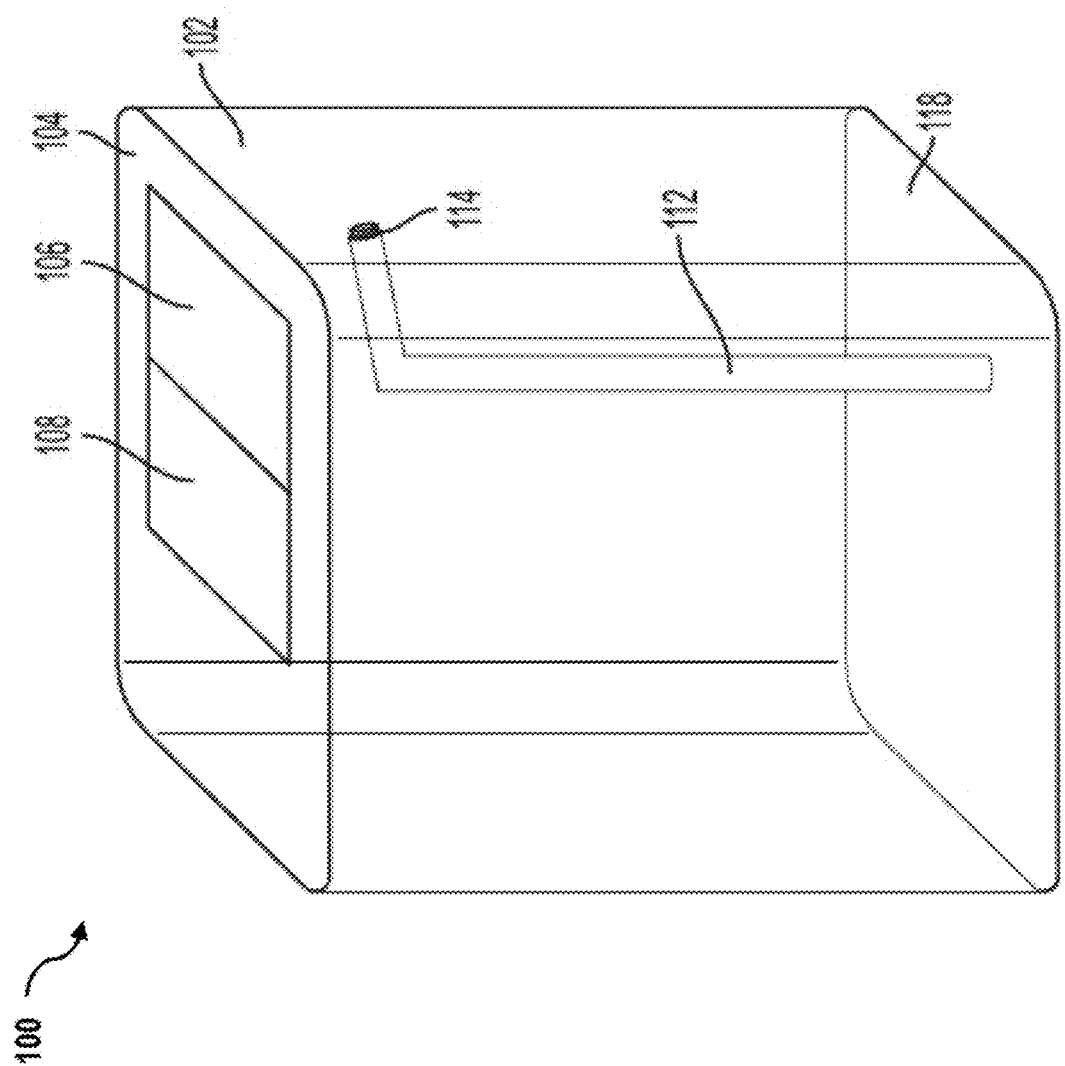
FIG. 5 is a perspective view of a medical waste container according to one embodiment described herein.
Figure 6:
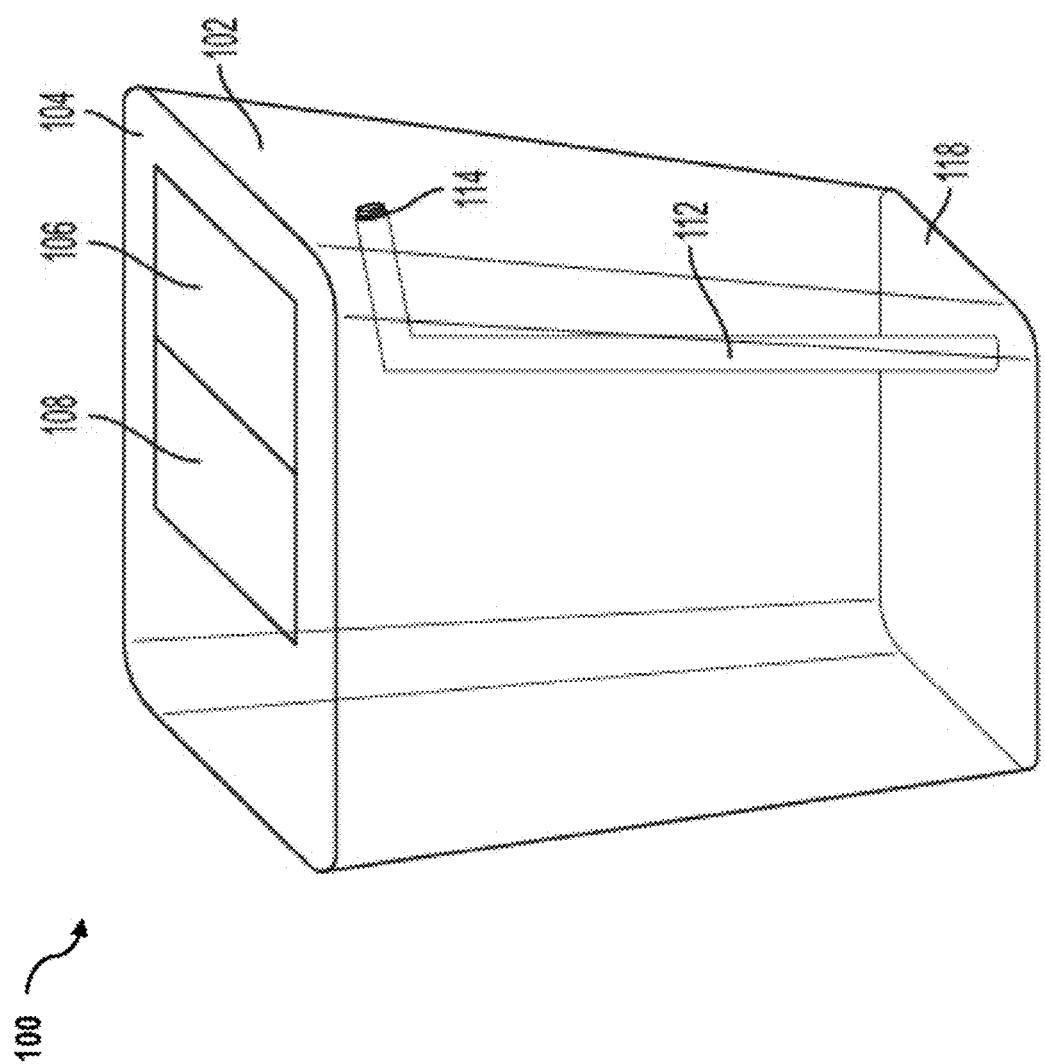
FIG. 6 is a perspective view of a medical waste container according to one embodiment described herein.

As shown in FIGS. 5 and 6, in some embodiments, the port 114 may be positioned in one of the at least one sidewalls of the vessel 102. Optionally, the port 114 may be positioned in the top portion of one of the sidewalls of the vessel 102. The tube 112 may be angled to direct fluid from the implement from the port 114 in a general horizontal direction toward the bottom of the vessel 102 in a general vertical direction.

Figure 7:
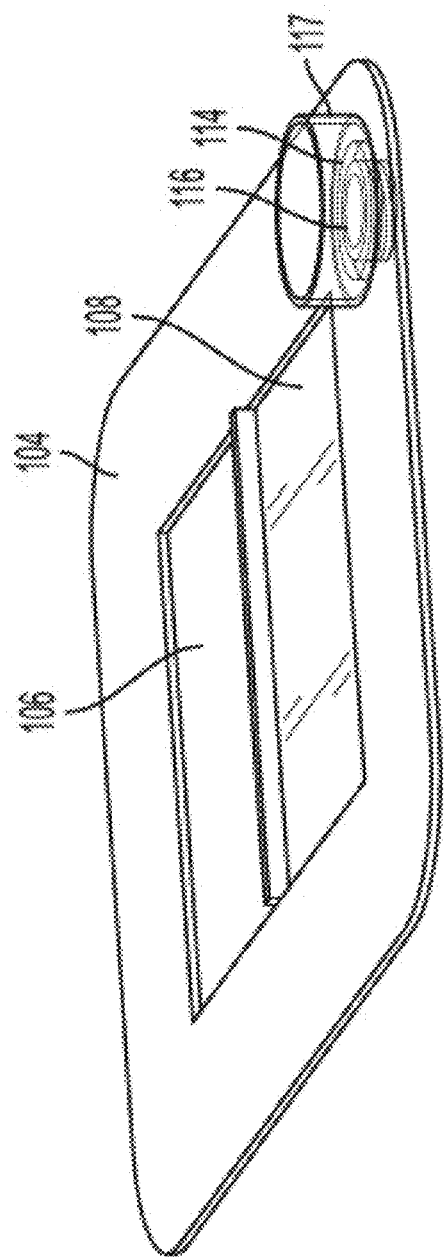
FIG. 7 is a perspective view of the top of a medical waste container according to one embodiment described herein.

As shown in the top view of FIG. 7, in certain embodiments, the container 100 may comprise a shield 117 that surrounds the port 114 and adaptor 116. The shield 117 may provide additional protection from inadvertent spray or splatter from the implement as fluid is disposed through the port 114 into the container 100.

Figure 8:
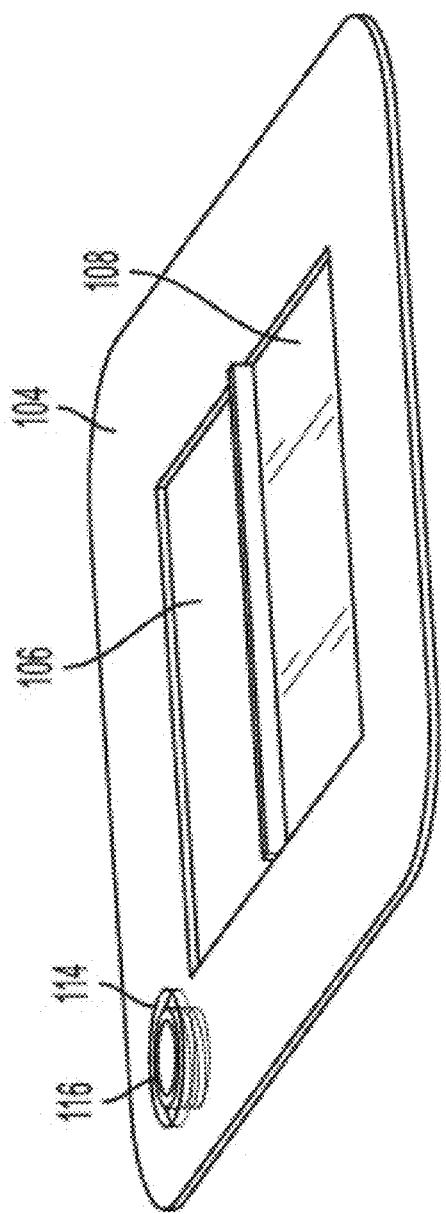
FIG. 8 is a perspective view of the top of a medical waste container according to one embodiment described herein.

The location of the port may vary in different embodiments. The port may be positioned at a first end of the cover and the opening may be positioned at a second end of the cover. The port 114 and opening 106 may be positioned at opposing ends of the cover as shown in FIG. 7. The port 114 and opening 106 may be positioned adjacent to each other in the cover 104 as shown in FIG. 8. In some embodiments, the port 114 may be placed in a corner of the cover 104. In other embodiments, the port 114 may be placed adjacent to the opening 106 or gate 108. In some embodiments, the port may be positioned in the at least one sidewall. Optionally, the port may be positioned in an upper end of the at least one sidewall.

Figure 9:
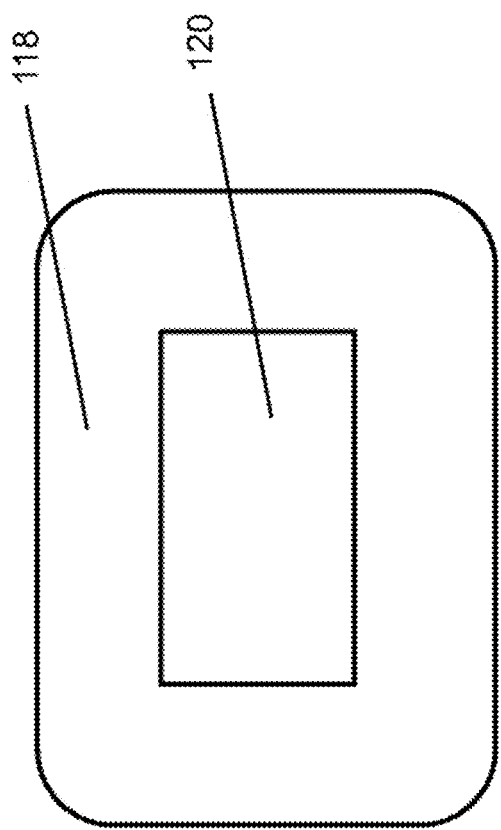
FIG. 9 is a top view of the bottom of a medical waste container according to one embodiment described herein.

In some embodiments, a container may comprise an absorbent material within an interior volume of the vessel. As shown in FIG. 9, the absorbent material 120 may be located on the base 118 of the vessel 102. In some embodiments, the absorbent material may comprise a gel.

Figure 10:
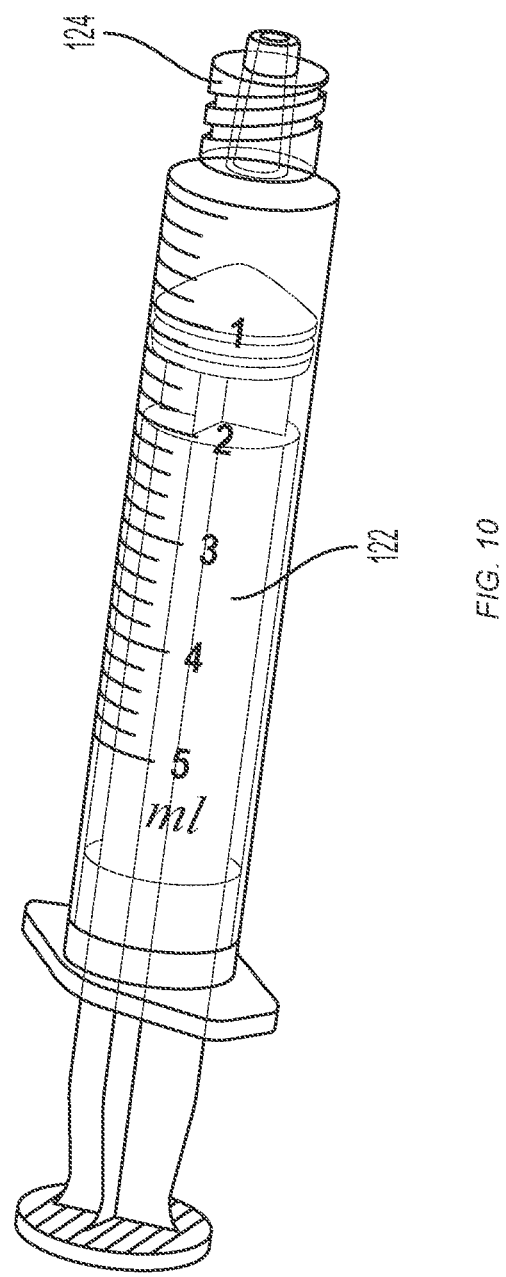
FIG. 10 is a perspective view of a medical implement according to one embodiment described herein.

Implements disposed of in medical waste containers can include a syringe, a hypodermic needle, a suture needle, a scalpel, used glass ampule, or any item considered sharp, In some cases, a syringe may include a threaded connection to attach a needle for injection into a patient. In other cases, a syringe may include a threaded connection to attach the syringe to an intravenous (IV) line of a patient. Some syringes may include "slip tip" that can insert into the rubber or silicone gasket in the end of an adapter and have no threads. As shown in FIG. 10, a syringe 122 may comprise a lock connection 124. In certain embodiments, the thread connection may be a Luer lock connection.

Figure 12:
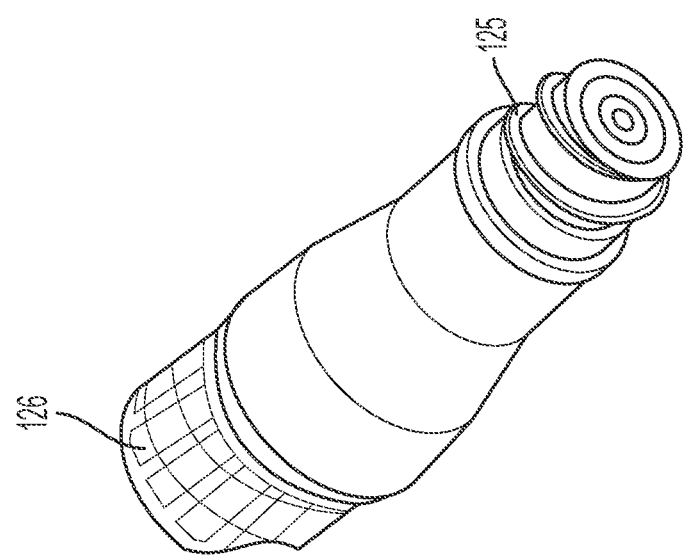
FIG. 12 is a perspective view of an adaptor for a medical waste container according to one embodiment described herein.
Figure 13:
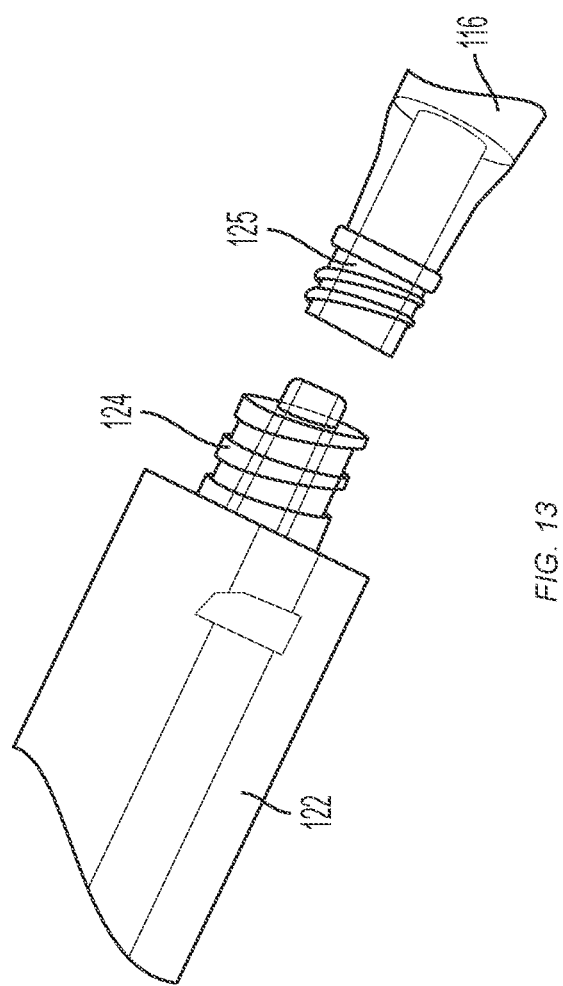
FIG. 13 is a side view of an adaptor for a medical waste container with an implement according to one embodiment described herein.

As shown in FIGS. 11 and 12, the adaptor 116 may be Luer lock compatible and comprise threads 125 that may be compatible with the Luer lock threaded end of a syringe. In some embodiments, a rigid or flexible tube may be connected to the adaptor 116 at end 126. The connection of threads 125 of an adaptor 116 with the lock connection 124 of a syringe 122 is shown in FIG. 13.

Implements disposed of in a waste medical container may comprise pharmaceutical compositions, such as narcotics or opioids. Implements disposed may comprise bodily fluids, for example, blood. In some cases, blood may be contaminated with infectious diseases. In some cases, an implement may comprise a pharmaceutical composition and a bodily fluid.

In other embodiments, the present disclosure comprises a method of using a waste container. The method may comprise discharging a fluid from an implement through a port into a vessel and disposing of the implement into the vessel through an opening defined by the cover. In some embodiments, the port may be positioned in a cover for the vessel. In other embodiments, the port may be positioned in a sidewall of a vessel. In some embodiments, the port may be coupled to a tube that extends into the vessel. In some embodiments, the tube may be rigid. In other embodiments, the tube may be flexible. Optionally, the method may further comprise connecting the implement to an adaptor on the port. In some cases, the adaptor may comprise a Luer lock or otherwise compatible with a discharge end of the implement. In certain embodiments, the port may be configured with a self-sealing valve in which the tip of the implement may be inserted to discharge remaining fluid into the container through the tube. In such cases, the method may comprise inserting the tip of the implement into the port, with optional adaptor, and discharging the contents of the implement. In some cases, the fluid may comprise a bodily fluid, a pharmaceutical composition, or a combination thereof.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

Various embodiments of the disclosure have been described herein. It should be recognized that these embodiments are merely illustrative of the present disclosure. Variations of those preferred embodiments may become apparent to those of ordinary skill in the art upon reading the foregoing description. It is expected that skilled artisans can employ such variations as appropriate, and the disclosure is intended to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated or otherwise clearly contradicted by context.

Illustrative Embodiments of Suitable Products and Methods

As used below, any reference to a series of illustrative products or methods is to be understood as a reference to each of those products or methods disjunctively (e.g., "Illustrative embodiments 1-4" is to be understood as "Illustrative embodiment 1, 2, 3, or 4").

Illustrative embodiment 1 is a waste container comprising a vessel comprising a base and at least one sidewall, wherein the at least one sidewall is connected to the base, wherein the at least one sidewall and base define an interior volume of the vessel, an absorbent material positioned within the interior volume of the vessel, a cover configured to connect to the at least one sidewall, a port having a first side and a second side, wherein the first side faces an exterior of the vessel and the second side faces the interior volume of the vessel, and a tube coupled to the second side of the port, wherein the tube is configured to direct a fluid from an implement toward the absorbent material Illustrative embodiment 2 is the container of any preceding or subsequent embodiment, wherein the base comprises a circular shape.

Illustrative embodiment 3 is the container of any preceding or subsequent embodiment, wherein the base comprises a polygonal shape.

Illustrative embodiment 4 is the container of any preceding or subsequent embodiment, wherein the vessel comprises four sidewalls.

Illustrative embodiment 5 is the container of any preceding or subsequent embodiment, wherein the cover has a complementary shape to the sidewalls and interior volume of the vessel.

Illustrative embodiment 6 is the container of any preceding or subsequent embodiment, wherein the cover defines an opening and the vessel is configured to receive a plurality of implements through the opening.

Illustrative embodiment 7 is the container of any preceding or subsequent embodiment, wherein the cover comprises a gate configured to substantially seal the opening in a first position and provide access to the interior volume of the vessel in a second position.

Illustrative embodiment 8 is the container of any preceding or subsequent embodiment, wherein the gate slides or rotates from the first position to the second position.

Illustrative embodiment 9 is the container of any preceding or subsequent embodiment, wherein the port is positioned in the cover.

Illustrative embodiment 10 is the container of any preceding or subsequent embodiment, wherein the port is positioned at a first end of the cover and the opening is positioned at a second end of the cover.

Illustrative embodiment 11 is the container of any preceding or subsequent embodiment, wherein the port and opening are positioned adjacent to one other in the cover.

Illustrative embodiment 12 is the container of any preceding or subsequent embodiment, wherein the port is positioned in the at least one sidewall.

Illustrative embodiment 13 is the container of any preceding or subsequent embodiment, wherein the port is positioned in an upper end of the at least one sidewall.

Illustrative embodiment 14 is the container of any preceding or subsequent embodiment, wherein the port comprises an adaptor compatible with a discharge end of the implement.

Illustrative embodiment 15 is the container of any preceding or subsequent embodiment, wherein the adaptor comprises a Luer Lock.

Illustrative embodiment 16 is the container of any preceding or subsequent embodiment, further comprising a shield around the port.

Illustrative embodiment 17 is the container of any preceding or subsequent embodiment, wherein the absorbent material comprises a gel.

Illustrative embodiment 18 is the container of any preceding or subsequent embodiment, wherein the cover is removable from the vessel.

Illustrative embodiment 19 is the container of any preceding or subsequent embodiment, wherein the tube is substantially perpendicular to the base.

Illustrative embodiment 20 is the container of any preceding or subsequent embodiment, wherein a length of the tube is less than a height of the at least one sidewall as measured substantially perpendicular to the base.

Illustrative embodiment 21 is the container of any preceding or subsequent embodiment, wherein the base is substantially rectangular, and the tube is adjacent to two sidewalls, placing the tube vertically in a corner of the vessel.

Illustrative embodiment 22 is the container of any preceding or subsequent embodiment, wherein the implement is a syringe.

Illustrative embodiment 23 is the container of any preceding embodiment, wherein the fluid comprises a bodily fluid, a pharmaceutical composition, or a combination thereof.

Illustrative embodiment 24 is a method of using a waste container, comprising discharging a fluid from an implement through a port into a vessel, wherein the port is positioned in a cover for the vessel, and the port is coupled to a tube that extends into the vessel and disposing of the implement into the vessel through an opening defined by the cover.

Illustrative embodiment 25 is the method of any preceding or subsequent embodiment, further comprising connecting the implement to an adaptor positioned on the port, wherein the adaptor is compatible with a discharge end of the implement.

Illustrative embodiment 26 is the method of any preceding embodiment, wherein the fluid comprises a bodily fluid, a pharmaceutical composition, or a combination thereof.

What is claimed is:

1. A waste container comprising:
   a vessel comprising a base and at least one sidewall, wherein the at least one sidewall is connected to the base, wherein the at least one sidewall and base define an interior volume of the vessel;
   an absorbent material positioned within the interior volume of the vessel;
   a cover configured to connect to the at least one sidewall;
   a port having a first side and a second side, wherein the first side faces an exterior of the vessel and the second side faces the interior volume of the vessel;
   a shield around the port; and
   a tube coupled to the second side of the port, wherein the tube is configured to direct a fluid from an implement toward the absorbent material.

2. The container of claim 1, wherein the base comprises a circular shape.

3. The container of claim 1, wherein the base comprises a polygonal shape.

4. The container of claim 1, wherein the cover has a complementary shape to the sidewalls and interior volume of the vessel.

5. The container of claim 1, wherein the cover defines an opening and the vessel is configured to receive a plurality of implements through the opening.

6. The container of claim 5, wherein the cover comprises a gate configured to substantially seal the opening in a first position and provide access to the interior volume of the vessel in a second position.

7. The container of claim 6, wherein the gate slides or rotates from the first position to the second position.

8. The container of claim 5, wherein the port is positioned in the cover.

9. The container of claim 8, wherein the port is positioned at a first end of the cover and the opening is positioned at a second end of the cover.

10. The container of claim 8, wherein the port and opening are positioned adjacent to one other in the cover.

11. The container of claim 1, wherein the port is positioned in the at least one sidewall.

12. The container of claim 1, wherein the port comprises an adaptor compatible with a discharge end of the implement.

13. The container of claim 12, wherein the adaptor comprises a Luer Lock.

14. The container of claim 1, wherein the absorbent material comprises a gel.

15. The container of claim 1, wherein the implement is a syringe.

16. The container of claim 1, wherein the fluid comprises a bodily fluid, a pharmaceutical composition, or a combination thereof.

17. A method of using a waste container, comprising:
   discharging a fluid from an implement through a port into a vessel, wherein the port is positioned in a cover for the vessel, and the port is coupled to a tube that extends into the vessel; and
   disposing of the implement into the vessel through an opening defined by the cover.

18. The method of claim 17, further comprising connecting the implement to an adaptor positioned on the port, wherein the adaptor is compatible with a discharge end of the implement.

19. The method of claim 17, wherein the fluid comprises a bodily fluid, a pharmaceutical composition, or a combination thereof.

20. A waste container comprising:
   a vessel comprising a base and at least one sidewall, wherein the at least one sidewall is connected to the base, wherein the at least one sidewall and base define an interior volume of the vessel;
   an absorbent material positioned within the interior volume of the vessel;
   a cover configured to connect to the at least one sidewall;
   a port positioned in the at least one sidewall, the port having a first side and a second side, wherein the first side faces an exterior of the vessel and the second side faces the interior volume of the vessel; and
   a tube coupled to the second side of the port, wherein the tube is configured to direct a fluid from an implement toward the absorbent material.

\* \* \* \* \*